(12) United States Patent
Speak

(10) Patent No.: US 7,553,303 B2
(45) Date of Patent: Jun. 30, 2009

(54) LOWER TORSO GARMENT HAVING LATERAL SLOT FOR EXTRACTION OF ABSORBENT ARTICLES THEREFROM

(76) Inventor: Jane Speak, 19173 SE. Fearnley Dr., Tequesta, FL (US) 33469

( * ) Notice: Subject to any disclaimer, the term of this patent is extended or adjusted under 35 U.S.C. 154(b) by 0 days.

(21) Appl. No.: 11/188,176

(22) Filed: Jul. 22, 2005

(65) Prior Publication Data
US 2007/0021728 A1   Jan. 25, 2007

(51) Int. Cl.
  *A61F 13/15*   (2006.01)
  *A61F 13/20*   (2006.01)
  *A41B 9/00*   (2006.01)
  *A41B 9/08*   (2006.01)

(52) U.S. Cl. .................. 604/385.14; 604/385.19; 604/400; 604/402; 2/78.2; 2/408

(58) Field of Classification Search ............ 604/385.14, 604/385.19, 393, 395, 400–402; 2/78.2, 2/408, 720
See application file for complete search history.

(56) References Cited

U.S. PATENT DOCUMENTS

| | | | |
|---|---|---|---|
| 3,459,181 A | 8/1969 | Mann | |
| 4,019,517 A | 4/1977 | Glassman | |
| 4,022,210 A | 5/1977 | Glassman | |
| 4,072,150 A | 2/1978 | Glassman | |
| 4,695,279 A | 9/1987 | Steer | |
| 6,102,899 A * | 8/2000 | Yimin | 604/385.01 |
| 6,415,450 B1 | 7/2002 | Lien | |
| 6,752,797 B2 * | 6/2004 | Oba | 604/395 |
| 2002/0165515 A1 * | 11/2002 | Burnham | 604/385.14 |
| 2004/0030314 A1 * | 2/2004 | LaVon et al. | 604/380 |

* cited by examiner

*Primary Examiner*—Melanie J Hand
(74) *Attorney, Agent, or Firm*—McHale & Slavin, P.A.

(57) ABSTRACT

A garment for the lower torso adapted to contain absorbent pads in the crotch region within the garment includes at least one laterally-oriented aperture therein for extraction or insertion of the pads and also for providing access for cleansing the soiled areas. The aperture can be either in the front or the rear of the garment, or both. The garment can support multiple pads in the crotch region in a stacked arrangement. The aperture is preferably either trapezoidal or formed from an arc-shaped cut and is constructed as a cut-out flap for selective access to the aperture. The novel aperture advantageously allows an absorbent pad to be extracted or inserted by the wearer or caregiver without removal of the undergarment or repositioning of the wearer from a prone or seated position.

12 Claims, 5 Drawing Sheets

LOWER TORSO GARMENT HAVING LATERAL SLOT FOR EXTRACTION OF ABSORBENT ARTICLES THEREFROM

FIELD OF THE INVENTION

The present invention relates generally to an improvement to a diaper or undergarment adapted to contain absorbent pads, and more particularly to the inclusion of a novel slot that allows the insertion and/or extraction of absorbent pads for urinary, menstrual or fecal wastes contained therein and also to allow access to cleanse the area without removal of the garment.

BACKGROUND OF THE INVENTION

There are numerous examples of diapers and diaper-type garments in the prior art intended for users having a wide variety of elimination needs. Infants, of course, have to wear a diaper or similar article until they are toilet trained. Specialized garments such as diapers and the like are often used by adult patients who are bedridden or otherwise infirm who are not able to use regular toilet facilities or who have lost control of their bodily functions. In addition, various types of absorbent garments are used by adults, who are incontinent due to physical illnesses such as bladder or urinary disorders, prostate problems, or senility.

A caregiver may find it difficult to change or replace a diaper or similar garment when a patient is in a prone or seated position because the patient's body must be raised to some extent in order to remove the soiled article. A patient who must wait for a caregiver to replace a wet pad or diaper not only risks infection, but also suffers loss of dignity. The caregiver must then escort the patient to the bathroom or make the change in bed. These are time-consuming and physically demanding activities for both parties. To address this problem, the present invention proposes a particularly shaped and sized slot that allows a soiled pad placed within the diaper to be withdrawn by the patient or caregiver without removal of the garment or repositioning a sitting or prone patient. This same benefit applies to infant diapers and toddler training pants.

DESCRIPTION OF THE PRIOR ART

U.S. Patent Appln. Pub. No. US2002/0165515 (Burnham) discloses a diaper comprising an impermeable outer shell, a means for securing it around the waist and legs, and a set of multiple absorbent pads located inside the shell. Each pad can be removed after use through slits in the shell, leaving behind a clean pad in its place for subsequent use and removal.

The Burnham diaper has numerous disadvantages. It is a disposable item that is not designed for replaceable pads. The vertically stacked openings for individual removal of pads require the soiled portion of all upper pads to be pulled across the wearer's abdomen during extraction. The narrow configuration of the openings causes the soiled portion of the pad to scrape against the opening, leaving a contaminated surface pressed against the wearer's body until the diaper is removed in its entirety. This constriction would also urge any solid fecal wastes to slide back on the pad and remain inside the diaper. Removal of a pad from the front pulls fecal contamination across the genital area and both urine and fecal matter across the pubic area up to the opening.

Another disadvantage of the Burnham diaper is that the protruding tongues on the pads for pad removal make it unsuitable for either adults without full mental acuity or infants. The pads extend from back to front within the wall of the diaper. During extraction of a pad, the wearer's weight must be lifted off the pad, or the wearer must stand up.

Glassman, in U.S. Pat. Nos. 4,072,150, 4,019,517, and 4,022,210, addresses the problem of fecal contamination in a diaper-type garment by providing a slot at the rear of the waist to enable a caregiver to push the pad over any fecal matter and a side tab for removal of the pad. As discussed above in connection with the diaper disclosed in the Burnham publication, drawbacks of the Glassman system include contamination of the wearer, the need to shift the weight of the wearer for removal of the pad, and limited access for cleansing the area.

U.S. Pat. No. 4,695,279, issued to Steer, discloses a pair of incontinence pants or briefs including a pocket located in the crotch region which has an outer wall of a liquid impermeable material such as rubber which is longer than it is wide and an inner wall whose edges define an oval hole. The inner and outer walls retain an elongated absorbent pad which may be withdrawn through the hole. This arrangement is suitable only for urinary or feminine sanitary pads, and would not be suitable as a garment to be used for bowel elimination needs. External removal of a soiled pad without contaminating the briefs is entirely dependent on the manual dexterity of the person removing the pad through the gap in the garment. This is not suitable for adults with poor coordination or without full mental acuity or children.

Thus, what is lacking in the art is a garment which can contain absorbent pads, either singly or in a stacked configuration, which allows the soiled pads to be extracted without removal of the garment and without contamination of the wearer's genital areas or the garment itself.

SUMMARY OF THE INVENTION

The present invention provides a pad extraction slot or aperture placed in the front and/or the back of the crotch of an undergarment for the purpose of extracting a single absorbent pad or the top pad in a layer of stacked absorbent pads without removal of the undergarment. The shape of the slot or aperture is an arc or a straight lateral cut intersecting with downwardly angled cuts which allows removal of the pad without contact of the soiled portion of the pad with the undergarment. The width of the slot will vary with the width needed for the pad to be removed without leakage of fluids contained within the pad. The height at the center of the slot will vary based on the thickness of the pad, the design of the pad, and the amount of vertical clearance desired.

Accordingly, it is an objective of the instant invention to provide a novel, laterally positioned aperture in a garment adapted to contain absorbent pads for children or adults for the removal and insertion of absorbent pads.

It is another objective of the instant invention to provide a slot or aperture in a garment adapted to contain absorbent pads which allows a caregiver to extract a soiled pad without removing the garment.

It is still another objective of the instant invention to provide a slot in a garment adapted to contain absorbent pads which provides access for a caregiver to cleanse soiled areas.

It is a further objective of the instant invention to provide a garment having an appropriately placed aperture which permits extraction of an absorbent pad contained therein without scraping the pad or contaminating the wearer with bodily wastes.

It is still another objective of the instant invention to provide a slot in a garment adapted to contain absorbent pads which has angled cuts which hold the side edges to keep the pad at the base of the slot and allow removal.

It is still another objective of the instant invention to provide a garment adapted to contain absorbent pads with an access slot having angled sides which position the pad at the base of the slot while it is being removed to avoid contamination of the garment.

It is yet another objective of the instant invention to provide a garment having a lateral pad extraction aperture which can accommodate a plurality of absorbent pads positioned in the crotch region in a stacked arrangement, so that soiled pads can be extracted one at a time.

It is a further objective of the present invention to provide a garment having a lateral pad extraction aperture which permits removal of the pad while the wearer is in a prone or seated position without the need to shift the weight or change the position of the wearer.

It is a still further objective of the invention to provide an undergarment having a lateral pad extraction aperture which can be can be manufactured either as a disposable or non-disposable item.

In accordance with the above objectives, a garment for the lower torso comprises a circular waist opening, a pair of leg openings defining a sagittal plane of the undergarment, and front panel and rear panels with a crotch region therebetween adapted to support absorbent pads within the undergarment. The garment can support multiple pads in the crotch region in a stacked arrangement. At least one of the front and rear panels includes a laterally-oriented aperture therein proximate the crotch region and symmetrical about the sagittal plane. The aperture is preferably trapezoidal or formed as a arc-shaped cut to provide a cut-out flap having a bottom edge perpendicular to the sagittal plane. The bottom edge is contiguous to the cut-out flap so that the cut-out flap can be extended and absorbent pads extracted or inserted through the aperture. The width of the aperture is determined by the size of the absorbent pad used with the garment. The aperture allows a single absorbent pad to be extracted without removal of the undergarment. The undergarment can be constructed from fabric, or can be a disposable item with an impermeable substrate layer with an absorbent material adhered thereto.

In an alternative embodiment, an undergarment for the lower torso includes a laterally-oriented aperture proximate the crotch region and symmetrical about a sagittal plane which is sized to allow extraction and insertion of absorbent pads therethrough. The undergarment further comprises a flap cover dimensioned to cover the aperture. The flap cover comprises a portion of resilient planar material having a perimeter wherein a portion of the perimeter is fixedly attached to the undergarment above the aperture. This allows the flap cover to hang freely over the aperture so that the aperture can be accessed by displacement of the flap cover.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention. The scope of the invention is defined by the claims appended hereto.

Figure 1:
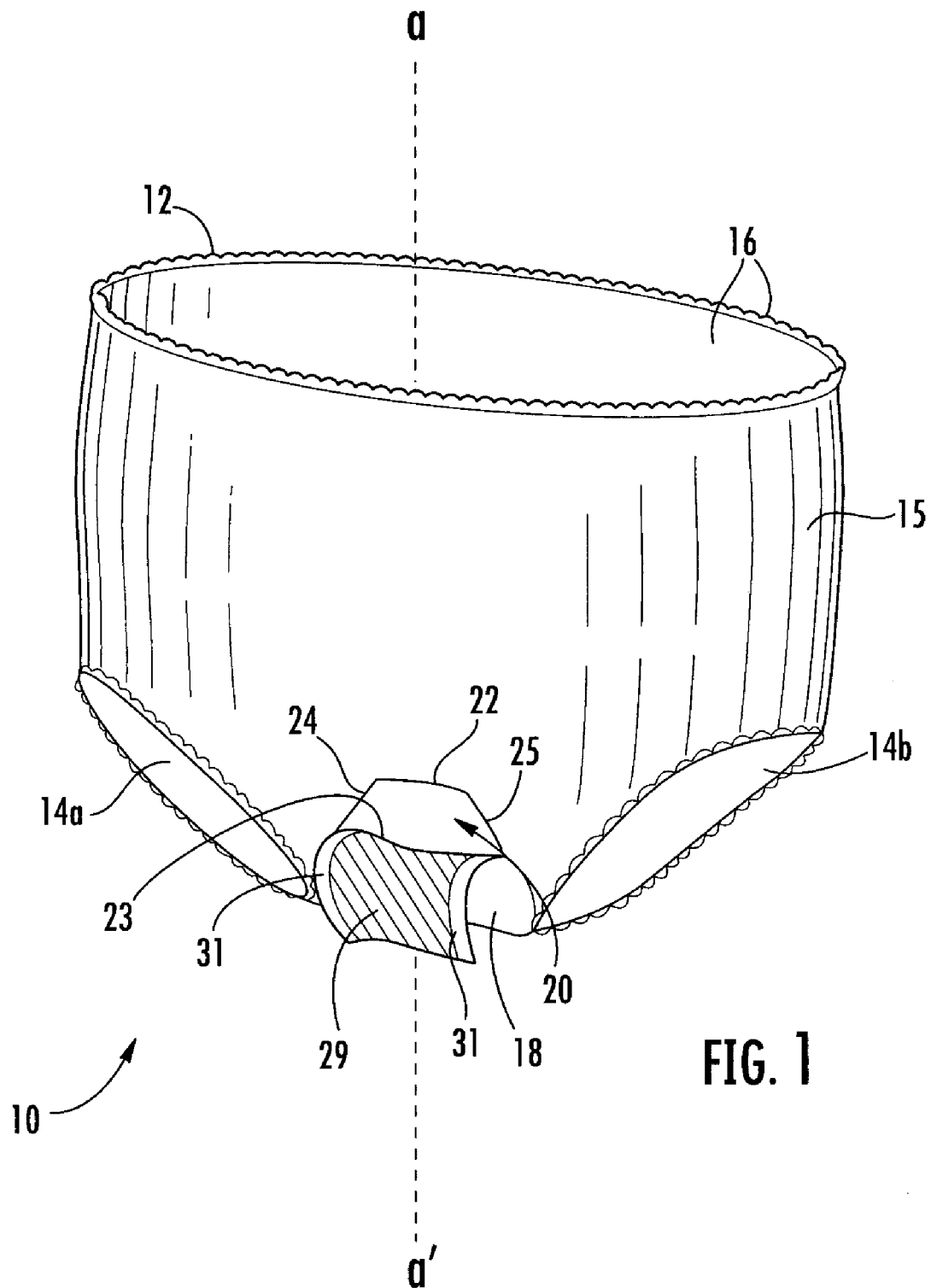
FIG. 1 is a perspective view of the undergarment according to a preferred embodiment of the invention showing the cut-out flap as placed in an open configuration to provide an aperture.

FIG. 1 is a perspective view of a preferred embodiment of a garment 10 of the invention including an improvement in accordance with the preferred embodiment of the invention. The garment 10 is for the lower torso and can be constructed from any suitable material to provide either a disposable diaper-type garment or a reusable, washable garment. The garment 10 includes a circular waist opening 12, and a pair of leg openings 14a and 14b which define the sagittal plane a-a' of the garment, i.e. the plane which divides the garment into left and right sides with reference to the corresponding sides of the wearer's body. The garment 10 has a front panel 15 and a rear panel 16, with a crotch region 18 therebetween adapted to support absorbent pads within the garment 10. At least one of the front and rear panels 15,16 includes a laterally-oriented aperture 20 therein proximate the crotch region 18 and symmetrical about the sagittal plane a-a'. The aperture 20 can be formed by a cut or slit in the garment. The aperture 20 can be located in either the front or rear panels 15,16, or alternatively, in both panels. Positioning the aperture 20 in the rear panel 16 is advantageous for removing fecal waste, or for limiting access so that the aperture 20 can only be used by a caregiver.

In the embodiment shown in FIG. 1, the aperture 20 is rectilinear in shape, with a top edge 22, a bottom edge 23 and opposing side edges 24,25. The aperture 20 is formed by providing a cut-out flap 29 which is contiguous to bottom edge 23. The top edge 22 and bottom edge 23 are perpendicular to the sagittal plane a-a'. In the illustrated embodiment, the aperture 20 is trapezoidal, with the top edge 22 having a length somewhat shorter that the bottom edge 23 with the opposing side edges 24,25 being angled symmetrical to one another.

Figure 2:
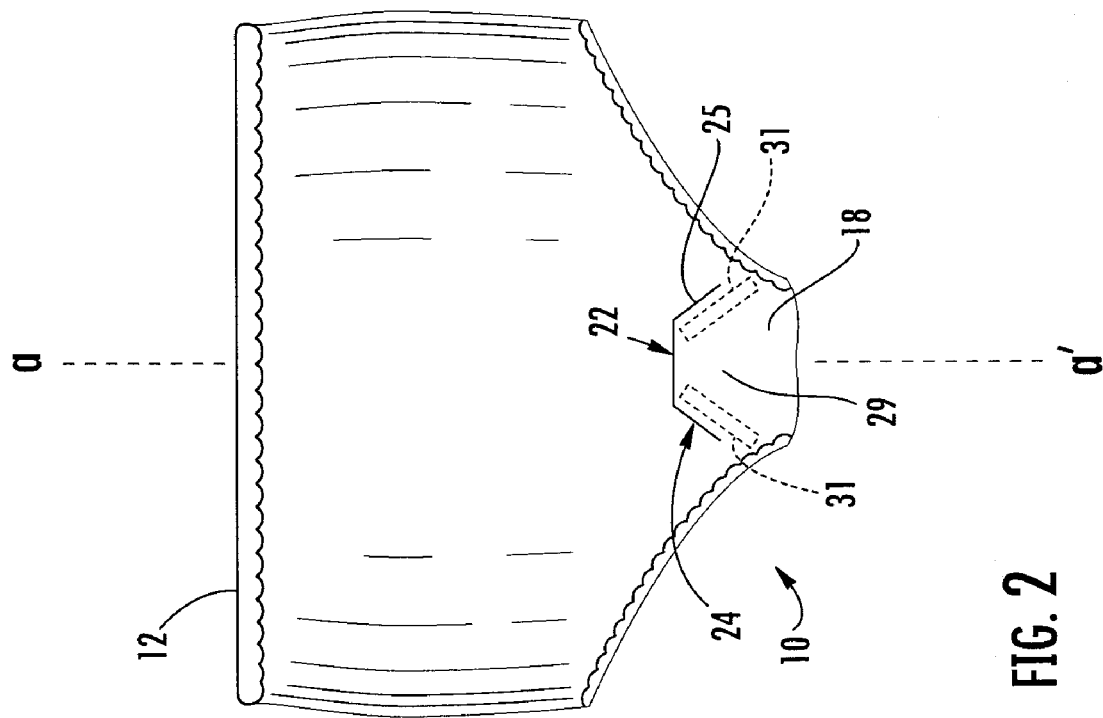
FIG. 2 is a front elevation view of the embodiment shown in FIG. 1 showing the cut-out flap in a closed configuration to close the aperture.

The cut-out flap 29 can be outwardly extended as shown in FIG. 1 to provide access to the aperture 20. As shown in FIG. 2, the aperture 20 can be partially sealed by moving the cut-out flap 29 to an upward position. To maintain the cut-out flap in an upward position, the garment 10 can include a pair of stays 31 of a semi-rigid material which are stitched or otherwise attached to the cut-out flap 29 in an approximately vertical orientation. Alternatively, other closure means can be used.

The trapezoidal configuration of the aperture 20 advantageously guides the pad during the extraction process so as to avoid soiling the garment because the angled opposing side edges 24,25 urge the pad toward the base of the aperture 20. In this way, a maximum clearance is maintained, making it less likely that the contents of the pad will be scraped by the top edge 22.

Figure 3:
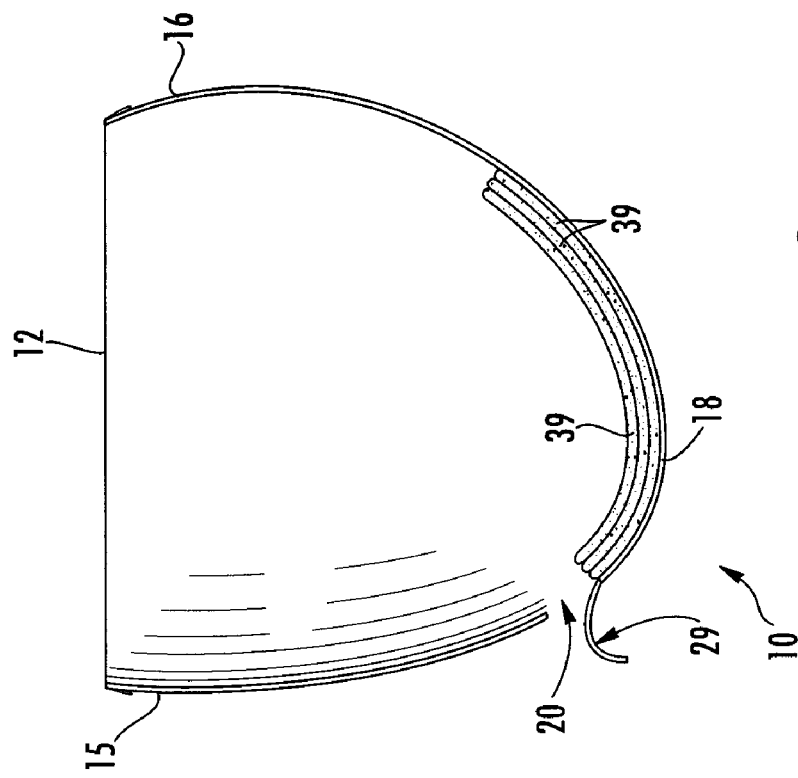
FIG. 3 is a left side cross-sectional view of the undergarment shown in FIG. 1 in which a plurality of absorbent pads in a stacked configuration are positioned within the undergarment.
Figure 5:
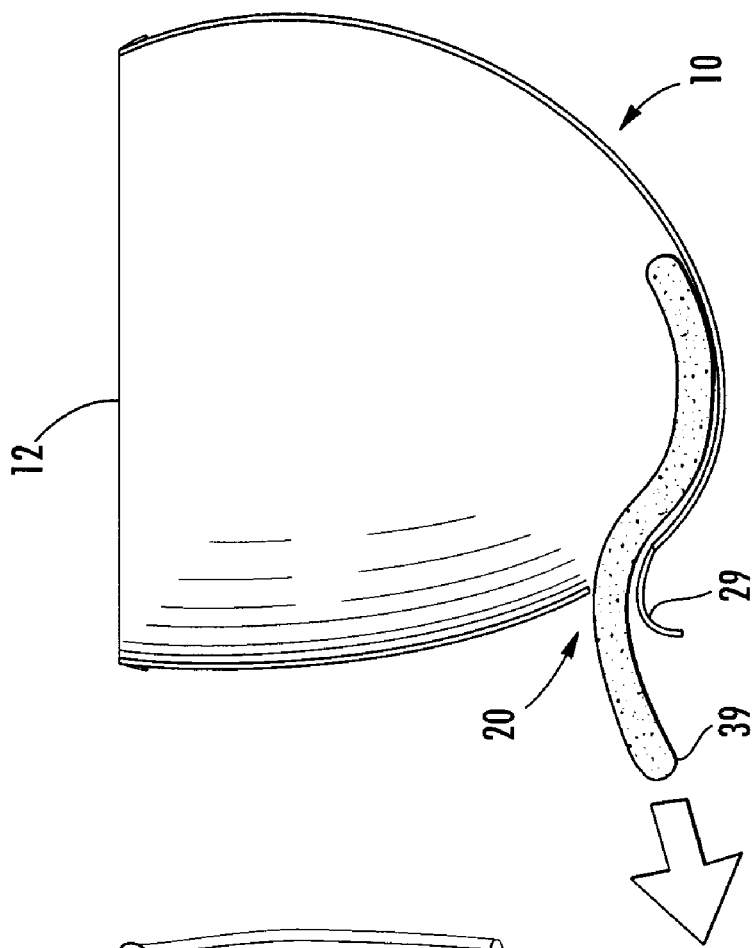
FIG. 5 is a side view showing a pad being extracted from the slot.
Figure 4:
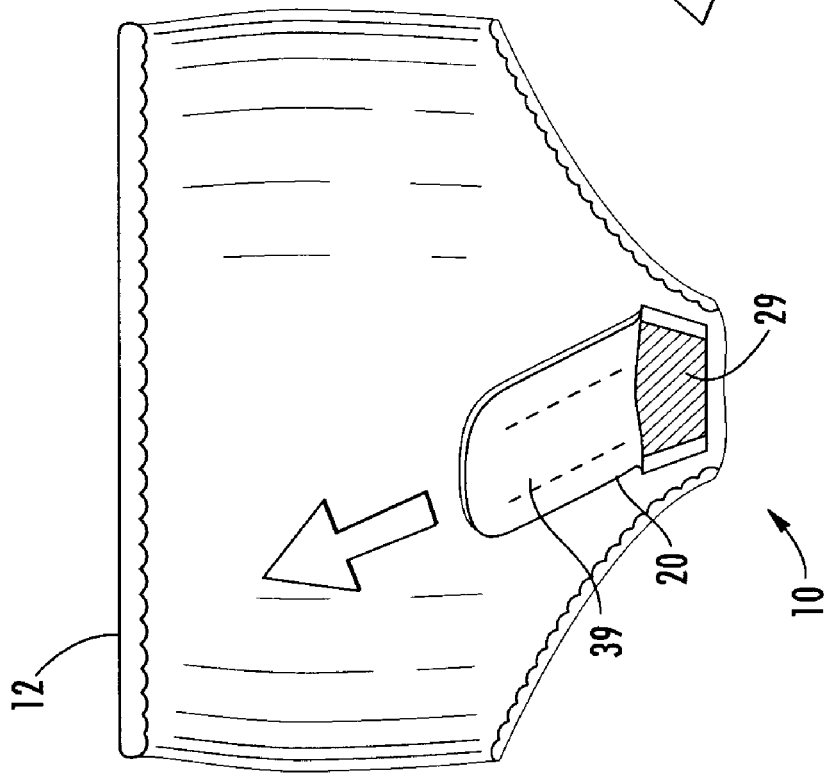
FIG. 4 is a front view showing a pad being extracted from the slot.

The width of the aperture 20 is determined by the size of the absorbent pad used with the garment 10. The aperture 20 allows a single absorbent pad to be extracted or inserted while the garment 10 is being worn without removal of the garment 10. The aperture 20 also provides access to cleanse the soiled area after a pad is removed. As shown in the cross-sectional side view in FIG. 3, the garment 10 can be constructed to contain multiple pads 39 in the crotch region 18 in a stacked arrangement. This arrangement allows a single pad to be extracted after it becomes soiled so that the underlying pad can then be used. The aperture 20 is preferably dimensioned to have a greater bottom width than top width and laterally disposed. In this way, the aperture 20 is aligned with the pad to be withdrawn, and it is not necessary to rotate the pad in any way. FIGS. 4 and 5 illustrate the operation of extracting a pad 39 from the slot 20.

The garment can be constructed from fabric, such as a woven material, to provide a garment which can be washed and reused. While it is not specifically depicted in the figures, the garment 10 can include a securement means around the waistline, such as an elastic band. The garment 10 can also be a disposable garment, which is nominally a diaper, constructed from a material having an outer impermeable substrate layer, such as plastic, with an absorbent material adhered thereto to provide the lining. It may be preferable to construct the garment 10 from a material having a sufficient rigidity for the cut-out flap 29 to be biased in the upward position until manually urged downward.

Figure 6:
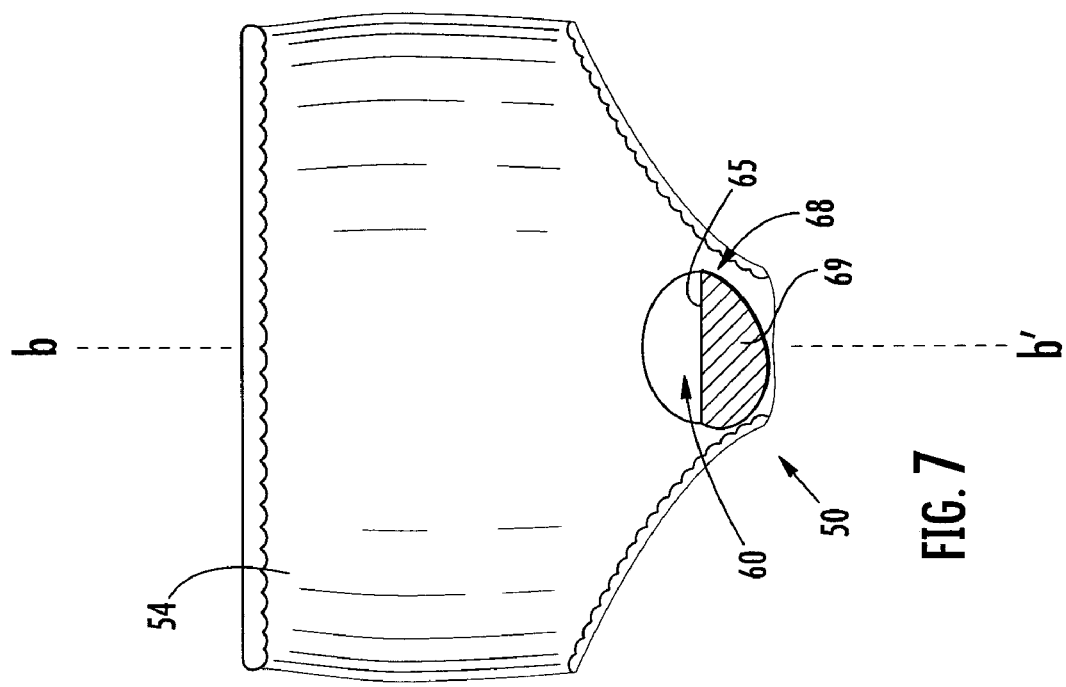
FIG. 6 is a front view of an alternative embodiment of the invention having cut-out flap formed from an arc-shaped cut in which the flap is in an closed configuration and the aperture is shown in phantom.
Figure 7:
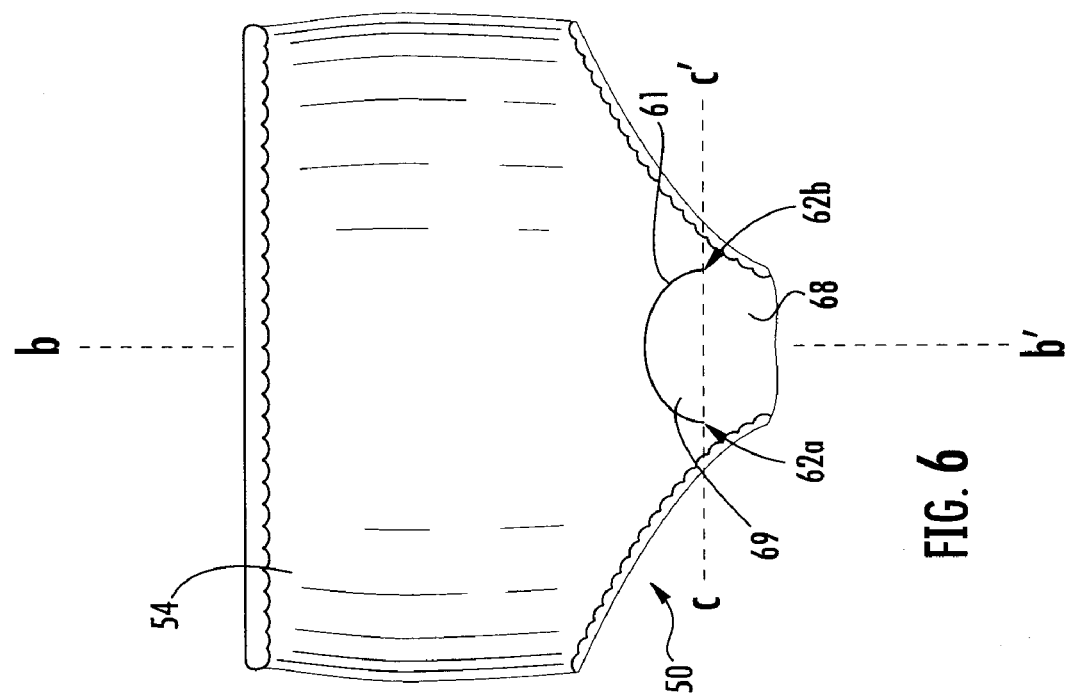
FIG. 7 is a front view of the embodiment shown in FIG. 4 in which cut-out flap in an open configuration to provide an aperture.

FIGS. 6 and 7 illustrate an alternative embodiment 50 of the garment of the invention. The garment 50 is similar in construction to the embodiment shown in FIGS. 1 and 2 in that it is symmetrical about a sagittal plane b-b'. As shown in FIGS. 6 and 7, the front panel 54 includes a laterally-oriented arc-shaped cut 61 therein which provides an aperture 60 proximate the crotch region 68 and symmetrical about the sagittal plane b-b'. The arc-shaped cut 61 has first and second ends 62a,b which define a line c-c' perpendicular to the sagittal plane b-b'. The line c-c' defines a bottom edge 65 of the aperture 60, with the bottom edge 65 being contiguous to the cut-out flap 69. The cut-out flap 69 can be extended and absorbent pads extracted or inserted through the aperture 69, and the arc-shaped configuration of the aperture 60 serves to guide the pad as it is extracted because the arc-shaped edges serve to urge the pad against the bottom edge 65.

The views shown in FIGS. 6 and 7 are described as front views for ease of description, however the rear view of the garment 60 can be identical to that of the front. The aperture 60 can be either in the front or rear of the garment, or both. As in the previous embodiment, the garment 60 can be constructed from either fabric so that garment can be washed and re-used. It can also be a formed from a conventional disposable diaper-type material having an impermeable outer shell.

Figure 9:
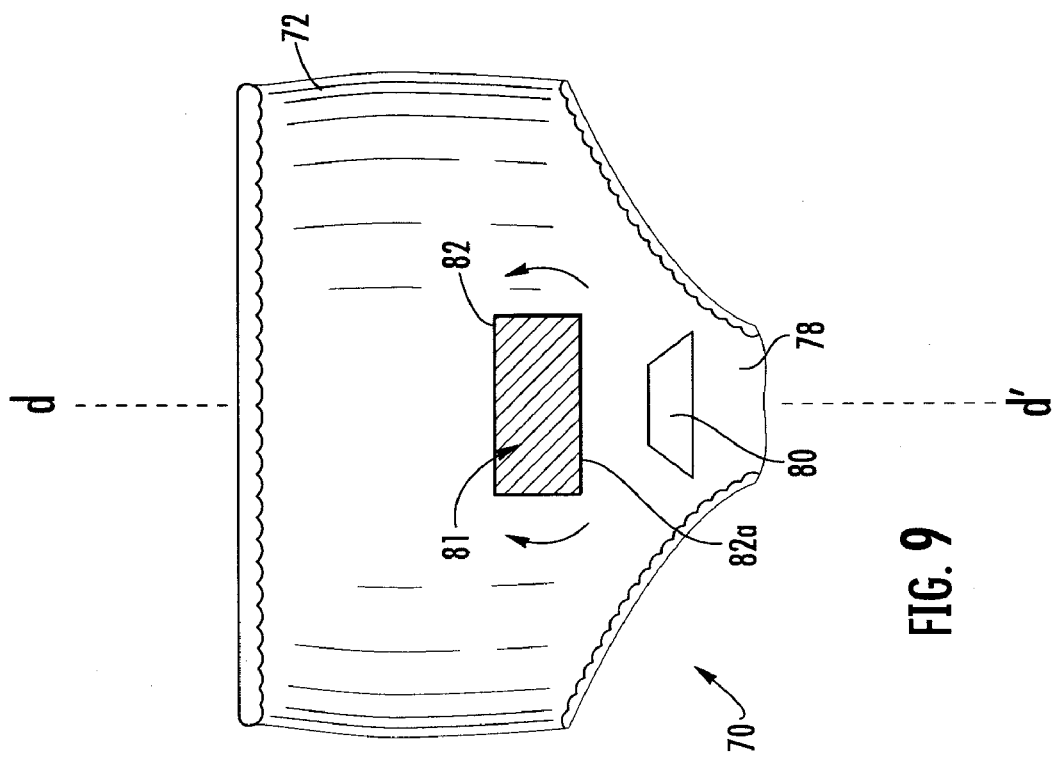
FIG. 9 is a front view of the embodiment shown in FIG. 6 in which the flap is lifted to provide access to the aperture.
Figure 8:
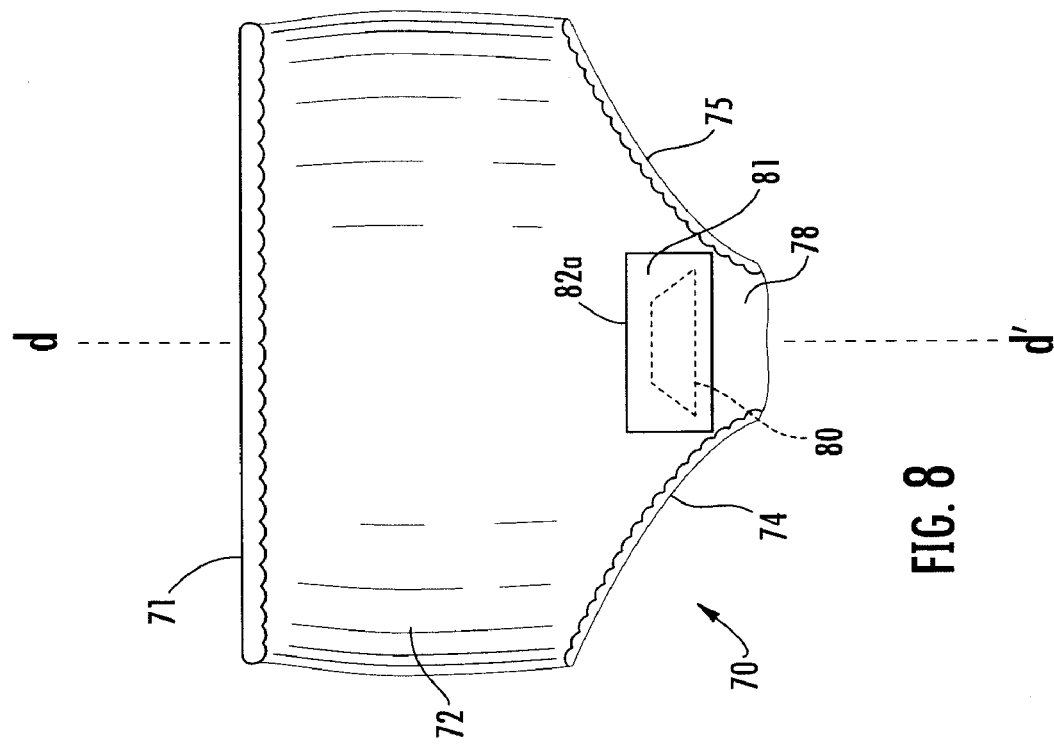
FIG. 8 is yet another alternative embodiment in which a flap is suspended over an aperture in the undergarment.

FIGS. 8 and 9 illustrate yet another embodiment of the invention. The garment 70 includes a circular waist opening 71, and a pair of leg openings 74 and 75 defining a sagittal plane d-d' of the garment. The view shown in FIGS. 8 and 9 can be either a front or rear view, however it is referred to as a front view herein for ease of description. The garment 70 has front panel 72 and a rear panel (not shown) with a crotch region 78 therebetween adapted to support absorbent pads within the garment. The front panel 72 includes laterally-oriented aperture 80 therein proximate the crotch region 78 and symmetrical about the sagittal plane d-d'. The aperture 80 is sized to allow extraction of an absorbent pad therethrough. In the illustrated embodiment, the aperture 80 has a trapezoidal shape, however the aperture 80 can have any desired shape, preferably one which has a greater bottom width than top width so as to align with the dimensions of the pad as it is being withdrawn so that minimal handling of the pad is required.

The garment 70 further includes a flap cover 81 dimensioned to hang over and cover the aperture 80 as shown in FIG. 8. The flap cover 81 is a portion of resilient planar material having a perimeter 82. A portion 82a of the perimeter 82 is fixedly attached to the garment by stitching, gluing, or other suitable attachment means at a point above the aperture 80. This allows the flap cover 81 to hang freely over the aperture 80 so that the aperture 80 can be accessed by manual displacement of the flap cover 81, as shown in FIG. 9. The flap cover 81 can also include a fastening means to secure it over the aperture 80, such as portions of hook and loop material, mated snaps, etc.

In each of the embodiments disclosed herein, the precise position of the aperture in the garment can be selected based on the intended use of the garment. For removal of pads for bowel waste, the aperture can be positioned in the rear of the garment. In the case of a garment designed for urinary incontinence or for menstrual needs, it is preferable to locate the aperture in the front of the garment. For infant diapers or for people with mental disabilities, the aperture can be placed towards the rear of the crotch to limit access so that the wearer cannot inappropriately tamper with the pad.

The garment 10 of the present invention advantageously allows the removal of a soiled pad without the removal of the garment, contamination of other body areas, contamination of the edges of the aperture, or requiring the wearer to shift weight or change from a prone or sitting position. The garment 10 can be sized to fit infants, children or adults.

Accordingly, the instant invention allows front removal of a soiled pad inserted in a diaper or undergarment without removal of the garment, contamination of other body areas or the removal slot, or requiring the wearer to shift their weight or change from a prone or sitting position. In use, loose outer garments (such as pants with an elastic waist or a skirt), allow the pad to be removed from the diaper-type garment without removal of the outer garments. The slot also provides access for cleansing the soiled area and inserting one or more replacement pads. Positioning a slot in the rear of the garment allows a caregiver to remove pads with fecal excrement from the rear.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

The invention claimed is:

1. In a garment adapted to contain absorbent pads therein having leg openings, a crotch region supporting a plurality of absorbent pads within said garment, and front and rear panels, comprising a laterallyoriented trapezoidal aperture in one of the front and rear panels, said aperture within the crotch region and formed as a cut-out flap and having top and bottom edges each having a length wherein said length of said top edge is less than said length of said bottom edge and said bottom edge is contiguous to said cutout flap, each said absorbent pad extending from said aperture along said crotch region to one of said front or rear panels positioned on said garment at an end of said crotch region opposite another end of said crotch region adjacent said aperture whereby said cutout flap is extended and said absorbent pads extracted and inserted through said trapezoidal aperture by the wearer without removal of the garment from the wearer, and said cutout flap further provides access for cleansing the nether regions of a wearer.

2. The garment of claim 1, wherein said aperture is positioned in both the front and rear panels.

3. A garment for the lower torso adapted for elimination needs comprising a circular waist opening, a pair of leg openings defining a sagittal plane of the garment, and front panel and rear panels with a crotch region therebetween supporting a plurality of absorbent pads within said garment, one of said front and rear panels including a laterally-oriented trapezoidal aperture therein within said crotch region and symmetrical about said sagittal plane, said aperture formed as a cut-out flap and having top and bottom edges perpendicular to said sagittal plane and each having a length wherein said length of said top edge is less than said length of said bottom edge and said bottom edge is contiguous to said cutout flap, each said absorbent pad extending from said aperture along said crotch region to one of said front or rear panels positioned on said garment at an end of said crotch region opposite another end of said crotch region adjacent said aperture whereby said cutout flap is extended and said absorbent pads extracted and inserted through said trapezoidal aperture without removal of said garment from the wearer, and said cutout flap further provides access for cleansing the nether regions of a wearer.

4. The garment of claim 3, wherein said crotch region of said garment supports said plurality of absorbent pads in a stacked arrangement.

5. The garment of claim 3, wherein said garment is constructed from fabric.

6. The garment of claim 3, wherein said garment is constructed from material comprising an impermeable substrate layer with an absorbent material adhered thereto.

7. The garment of claim 6, wherein said impermeable substrate is plastic.

8. A garment for the lower torso adapted for elimination needs comprising a circular waist opening, a pair of leg openings defining a sagittal plane of the garment, and front panel and rear panels with a crotch region therebetween supporting a plurality of absorbent pads within said garment, one of said front and rear panels including a laterally-oriented arcshaped cut therein within said crotch region and symmetrical about said sagittal plane, said arcshaped cut configured to provide an access aperture formed as cutout flap having a bottom edge perpendicular to said sagittal plane wherein said bottom edge is contiguous to said cut-out flap, each said absorbent pad extending from said aperture along said crotch region to one of said front or rear panels positioned on said garment at an end of said crotch region opposite another end of said crotch region adjacent said aperture whereby said cutout flap is extended and said absorbent pads extracted and inserted through said arc-shaped aperture without removal of said garment from and wearer, and said cut-out flap further provides access for cleansing the nether regions of a wearer.

9. The garment of claim 8, wherein said crotch region of said garment supports said plurality of absorbent pads in a stacked arrangement.

10. The garment of claim 8, wherein said garment is constructed from fabric.

11. The garment of claim 8, wherein said garment is constructed from material comprising an impermeable substrate layer with an absorbent material adhered thereto.

12. The garment of claim 11, wherein said impermeable substrate is plastic.

* * * * *